United States Patent [19]
Knoll

[11] Patent Number: 5,393,401
[45] Date of Patent: Feb. 28, 1995

[54] METHOD OF MANUFACTURING MINIATURIZED COMPONENTS OF CHEMICAL AND BIOLOGICAL DETECTION SENSORS THAT EMPLOY ION-SELECTIVE MEMBRANES, AND SUPPORTS FOR SUCH COMPONENTS

[76] Inventor: Meinhard Knoll, Geschwister-Scholl-Str. 9, 4430 Steinfurt-Burgsteinfurt, Germany

[21] Appl. No.: 966,148
[22] PCT Filed: May 6, 1992
[86] PCT No.: PCT/EP92/00990
§ 371 Date: Jan. 7, 1993
§ 102(e) Date: Jan. 7, 1993
[87] PCT Pub. No.: WO92/21020
PCT Pub. Date: Nov. 26, 1992

[30] Foreign Application Priority Data
May 10, 1991 [DE] Germany ............... 4115414

[51] Int. Cl.⁶ ............................................. G01N 27/26
[52] U.S. Cl. .................................. 204/418; 204/403; 204/414; 427/534; 427/289; 427/290; 427/307
[58] Field of Search ............ 204/403, 416, 418, 419, 204/414, 433, 435; 427/534, 581, 289, 290, 307

[56] References Cited

U.S. PATENT DOCUMENTS

| | | | |
|---|---|---|---|
| 4,645,562 | 2/1987 | Liao et al. | 427/534 |
| 4,874,499 | 10/1989 | Smith et al. | 204/403 |
| 5,111,221 | 5/1992 | Fare et al. | 204/418 |
| 5,183,549 | 2/1993 | Joseph et al. | 204/418 |

FOREIGN PATENT DOCUMENTS

0299778 7/1988 European Pat. Off. .
2236903 4/1991 United Kingdom .

*Primary Examiner*—John Niebling
*Assistant Examiner*—Bruce F. Bell
*Attorney, Agent, or Firm*—Karl F. Milde, Jr.

[57] ABSTRACT

The invention relates to a process for producing miniaturized chemical and biological sensor elements with ion-selective membranes. To simplify production in the micro range, an aperture (5,6) starting from the front (3) and tapering toward the back (4) is made in a thin silicon substrate (1) so that the front and back are interconnected. A liquid with which the ion-selective membrane is formed is poured into the containment (2) thus formed. Vertical ISFETs may also be made on the above principle.

33 Claims, 5 Drawing Sheets

METHOD OF MANUFACTURING MINIATURIZED COMPONENTS OF CHEMICAL AND BIOLOGICAL DETECTION SENSORS THAT EMPLOY ION-SELECTIVE MEMBRANES, AND SUPPORTS FOR SUCH COMPONENTS

BACKGROUND OF THE INVENTION

The invention concerns a method of manufacturing supports for miniaturized components of sensors that detect chemicals and biologicals by means of ion-selective membranes. The invention also concerns a method that employs the aforesaid supports to manufacture chemical and biological detection components and vertical ion-selective field-effect transistors (VISFET's). Finally, the invention concerns the chemical and biological detection sensor components manufactured by the aforesaid methods.

The manufacture of very small versions of microsensors that operate on the principle of ion-selective electrodes (ISE's) without liquid interior electrolytes is known. Electrodes with liquid membranes can be employed for example in accordance with what is called the coated-wire principle (P. Bergveld, "Development and Application of Chemical Sensors in Liquids," p. 403, in *Sensors and Sensory Systems for Advanced Robots*, Berlin and Heidelberg, Springer, 1988). A fine silver wire is coated with what is called an ion-selective liquid membrane. Such an electrode is tiny enough to be inserted in the blood vessels. Coated-film electrodes are manufactured by a similar process. The simplest coated-film electrode is a substrate of plastic covered with a thin coat of silver or silver chloride over silver and then with the ion-selective liquid membrane. Coated-film electrodes of this type can also be manufactured on a silicon substrate instead of a plastic substrate.

The manufacture of ion-selective liquid membranes is also known in itself. Such membranes can consist for example of a polyvinyl-chloride matrix that includes both a softener and an ionophore, an electrically active substance that dictates the membrane's ion selectivity. The material is dissolved and poured, and the solvent evaporates, leaving a solidified membrane. Examples will be evident from the sales literature *Selectophore Inonophores for Ion-Selective Electrodes*, published by Fluka Feinchemikalien GmbH, Neu-Ulm.

There are drawbacks, however, to known miniaturized sensors that operate on the ISE principle. First, the membrane adheres very poorly to the wire or layer of silver. Again, a phenomenon called bleed leads to impoverishment of the ionophore in the membrane. Electrochemical properties are lost and the change in composition can even impair the biocompatibility of a membrane intended for medical applications.

The same problems occur when ion-selective liquid membranes are employed at the gates of ion-selective field-effect transistors (ISFET's). The literature cites attempts to solve the adhesion problem with nets of polyimide and anisotropically etched silicon lids with narrow openings (Göpel, Hesse, and Zemel, eds., *Sensors*, Weinheim, VCH, 1989, Vol. 1, Chap. 4, pp. 97-99). All that the nets do, however, is solve the adhesion problem. The silicon lid is very difficult to position properly in areas measuring less than 0.1 mm across.

Integrating an ion-selective sensor component into an integrated circuit leads to additional problems relating to encapsulation. The silicon chip is tiny enough to confine the active surface of the membrane to the immediate vicinity of the fine bond filaments that electrically connect the chips to the sensor-housing contacts.

The literature reports attempts to solve the problem by positioning the contacts on the rear of the transistor (cf. e.g. Ewald, van den Berg, and Grisel, "Technology for Backside Contacted pH-sensitive ISFETs Embedded in a p-Well Structure," *Sensors and Actuators* 1 (1990), 335-40).

One drawback to such an approach is that, since the side of the chip with the delicate semiconducting signal-electronics structures is separated from the fluid being analyzed only by a thin inactivating layer, even a very slight contamination of the semiconductor structures will render the sensing electronics unusable. The aforesaid encapsulating problem in particular will occur not only in conjunction with ion-selective sensor components with liquid membranes but with those with other types of membrane (e.g. solid) in an integrated circuit.

SUMMARY OF THE INVENTION

Improvement will accordingly necessarily derive from a principle allowing the creation of ion-selective sensor components on silicon chips with liquid membranes, membranes of other types, electrochemically or biochemically relevant sensor-component coats obtained from the liquid phase, or solid membranes, and exhibiting the properties good membrane adhesion, minimal ionophore impoverishment in the liquid membrane, good potential for applying and microstructuring the membranes to silicon surfaces, high electric stability on the part of the ISFET structures employed, and ideal conditions for sensor-to-chip contact and encapsulation.

This object is attained by using supports manufactured by the method of (1) producing in a thin silicon substrate an opening that tapers together from the front to the back and provides communication between the front and the back, and (2) introducing a liquid into the resulting containment to form an ion-selective membrane. An ion-selective membrane can be manufactured in a vertical containment in these supports that has an opening to the back of the chip and is characterized by the following properties:

micromechanical anchoring and good lateral membrane microstructures due to the special containment geometry, a low quotient of active membrane surface and membrane volume to ensure a deposit effect and accordingly minimize membrane-ionophore impoverishment, an active membrane surface on the back of the silicon chip to ensure optimal contact-and-encapsulation conditions.

The invention also concerns introducing the membrane into the containment as specified hereinafter.

The containment itself can be manufactured in the silicon substrate by known micromechanical techniques, "anisotropic etching" for example. Anisotropic etching exploits known lithographic and masking processes to obtain depressions or holes for example in a (100)-oriented silicon-monocrystal wafer. Four-place symmetry results, with all (111) surfaces tilted 54.75°, in pyramidal depressions and holes The final dimensions of the starting opening depend on the type of mask, the thickness of the wafer, and precise awareness of the rate of etching in the (111) direction. Arrays of different depressions can accordingly also be obtained in a single wafer (Anton Heuberger, *Mikromechanik,* Berlin, Springer, 1989). A depression obtained by anisotropic etching is pyramidal, with a wide opening at one surface of the wafer and, when etched through to the other surface, a smaller opening there.

If the diameter of the narrower opening is $W_k$ and that of the wider opening is $W_g$, $$W_k = W_g - \sqrt{2} \cdot d$$

for (100)-oriented silicon substrates of thickness d (Heuberger, op. cit., p. 393). With the narrower openings typically measuring 1 to 100 μm and the wider openings occupying proportionally more of the chip real estate, the number of V-shaped containments that can be obtained in a (100)-oriented silicon substrate is accordingly limited.

Containments that occupy less real estate can be obtained in (110)-oriented silicon substrates. The two-place symmetry in these substrates results in more complicated containment geometries, however. With the etching masks correctly positioned in relation to the orientation of the substrate, some of the etch-demarcating (111)-crystal surfaces and hence the walls of the containment will be perpendicular while others will slope 35° to the surface of the substrate (Heuberger, op. cit., pp. 344–48 and 392–97).

Since the parallel and perpendicular walls of the etched-out containment are separated by very short distances $d_p$, on the order of a few microns, the containments will occupy much less of the chip's real estate. The actual real estate will be dictated by the aforesaid minimal distance $d_d$ and by the width of the etch pit perpendicular thereto as dictated in turn by the slope of the walls.

Very narrow through-etched openings with very precise tolerances can be obtained by coating the second surface of the silicon wafer with a layer of what is called resist, etching through to that area, and then opening the layer of resist where the opening narrows as far as the other surface of the wafer, from the back for example. This can also be done with known procedures, by additional selective lithography and masking followed by etching.

It is also possible to provide at least the vicinity of the openings in the depression on one surface of the wafer or the other and the inner surfaces of the containment with a continuous non-conducting layer of silicon dioxide by such known procedures as thermal oxidation, chemical-vapor deposition, sputtering, or sol-to-gel transformation. Since the high density of hydroxyl groups at the surfaces of a silicon-dioxide coating will lead to rejection of the liquid membrane (a polyvinylchloride membrane for example), the interfaces can be silanized to promote adhesion. Silanization is now common in the liquid-membrane field in relation to miniaturized glass electrodes (Daniel Ammann, *Ion-Selective Microelectrodes,* Berlin, Springer, 1986). Such materials as $Si_3N_4$, $Al_2O_3$, or $Ta_2O_5$, silicates of aluminum, boron, or sodium and aluminum, sol-to-gel transforms, etc. can be employed instead of silicon dioxide for the layers.

The particular advantage of such containments are that their geometries serve to micromechanically anchor the membranes into them and that very few such mobile constituents of the membrane as ionophores and softeners will bleed out because of the very low ratio of active membrane-surface area to volume.

The particular advantage of the method is that the aforesaid containments are obtained with procedures known and highly developed in the processing of microchips.

Contact between the membrane and the silicon chip's signal-electronics amplifier and impedance converter components can be established by modifications of three strategies—coated film, half cells, or ISFET's.

In the modified coated-film approach the membrane will be in direct contact with a coat of silver or silver chloride over silver that covers part of the inner wall of the containment.

Other appropriate electrically conductive materials can also be employed for the coating.

The principle of the ion-selective field-effect transistor (ISFET) was developed on the basis of planar metal-oxide semiconductor field-effect transistors (MOSFET's: Bergveld, op. cit., p. 407) and is modified in accordance with the invention modifed on the principle of the vertical MOSFET's.

The known vertical-MOSFET design (R. Paul, *Elektronische Halbleiterbauelemente,* Teubner Studienskripten, Stuttgart, Teubner, 1986, p. 336) is modified by etching the V pit through to the back of the chip, creating the containment r for the ion-selective membrane. The membrane replaces the gate contact.

The result is a vertical ion-selective field-effect transistor (VISFET) that exploits all the advantages of the specially shaped membrane containment.

Vertical ISFET structures (VISFET's) can be designed on the analogy of other known vertical MOSFET's, with reversed n and p doping, different epitaxial-layer dispositions, and different pit geometries (U-shaped e.g.).

The present invention also expressly concerns a vertical ISFET (VISFET), which has a vertical containment and an ion-selective membrane that has its active surface at the back of the chip.

The polymeric membrane, the liquid membrane, and other electrochemically relevant coating materials (e.g. hydrogels) obtained from a liquid phase can be introduced with an automatic syringe. The liquid is introduced through the wider opening. After an interval that depends on the material employed, the solvent evaporates and the solidified membrane occurs in the containment. If a solid electrolyte is employed as well, it can be applied over the membrane in the form of an additional layer from the liquid phase.

When very small containments like those that can be obtained on (110)-oriented silicon substrates are employed or when the area of the chip is very small, it can be of definite advantage to introduce the membrane liquid into the containment indirectly. An additional depression (filling chamber) with a capillary channel communicating with the containment is created on the wafer by one of the aforesaid micromechanical procedures (anisotropic etching for example). The filling opening can be far enough from the sensor component to be separated when the chips are isolated by breaking up the wafer. The product is very tiny sensor chips with no extra real estate taken up by filling openings.

Membrane liquid can also be introduced into several or all of the containments in a single wafer simultaneously through one filling opening with many capillary communicating channels. Flow can be improved by introducing the liquid in a solvent atmosphere.

This aforesaid filling approach represents a "full-wafer process" for obtaining liquid membranes and other types of layer from the liquid phase.

The ion-selective membranes that form in the containments can be protected by another layer of material (e.g. silicone or epoxide). The layer can protect each containment separately, a whole chip, or the whole wafer.

Ion-selective sensor components of the aforesaid type can also be employed as biological-detection sensors. An enzyme for example can be immobilized in the membrane. The membrane could also contain antibodies, microbes, or organelles for example. In the simplest case the materials are added to the liquid before it is introduced into the containment.

Such components can be employed to detect glucose, penicillin, urea, etc. in liquids (Peter Hauptmann, *Sensoren,* Munich, Carl Hanser, 1991, pp. 124–28).

Once the wafers have been isolated into chips, the sensor components can be accommodated in housings or enclosed in plastic. It is particularly practical for the active membrane surfaces to be on the other side of the chip from the delicate semiconductor circuitry and its fine bond filaments.

The invention will now be described with reference to the accompanying drawings.

DESCRIPTION OF THE PREFERRED EMBODIMENTS

Figure 1:
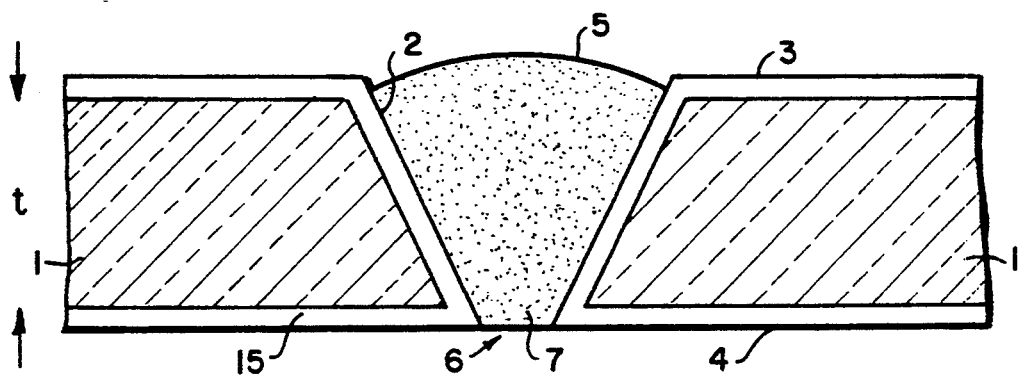
FIG. 1 is a section through part of a sensor chip with an ion-selective membrane in a microstructured containment, FIG. 2 a section showing a covered membrane, FIG. 3 a section showing a containment manufactured using a layer of resist, FIG. 4 an ion-selective sensor component in accordance with the "coated-film principle,"

FIG. 1 is a section through part a sensor chip manufactured on a silicon wafer. The thickness t of the (100)-oriented for example wafer is between 0.1 and 1 mm. A containment 2 in the form of a pyramidal depression has been etched in the crystal's (100) direction into an area precisely defined by known masking techniques. The pyramid has an apical angle of 54.75° in direction (111). The etching proceeds from one surface 3 and extends through to the opposing parallel surface 4. For simplicity's sake surface 3 will be considered the top and surface 4 the bottom hereinafter.

If the wafer has a (110) instead of a (100) orientation, it must be positioned in relation to the mask to ensure that as hereintofore mentioned the etching will produce two opposing perpendicular walls and two sloping walls in the containment. If the distance between the two parallel walls is very short (on the order of a few microns), the containment opening will occupy very little of the chip's real estate. The section in FIG. 1 would in this event parallel the perpendicular walls of the containment.

Two openings 5 and 6 that penetrate top 3 and bottom 4 with diameters that relate in the aforesaid way will accordingly occur. The diameter of opening 6 ranges between $10^{-4}$ and $10^{-1}$ mm.

The containment can be etched out with potassium hydroxide or other known agents (cf. Heuberger, op. cit., pp. 125–1609).

All or part of the silicon surface can be coated, after the containment has been etched, by known thermal-oxidation, chemical-vapor deposition, or spin-on-glass methods with a layer 15 of silicon dioxide. The layer can be silanized for the aforesaid reasons. The layer also covers the walls of the containment. Layers of materials (e.g. $Si_3N^4$) other than silicon dioxide can also be applied by the aforesaid procedures.

The wafer, with one or conventionally several containments 2 is then positioned on an annular surface, leaving the openings free. It is, however, also possible to lay the wafer on a plane polished plate. Microscopic portions of a solution that turns into an ion-selective membrane are now injected into containment 2 by an unillustrated device. If the containment's bottom opening is left open while the membrane liquid is being introduced, the solution's surface tension and the narrowness of the opening will keep it in the containment. A solution for manufacturing an ion-selective membrane can be a known solution of polyvinyl chloride, a softener, and an ionophore in tetrahydrofuran. Precise recipes for such solutions are provided in the aforesaid Fluka literature. Other membrane materials that can be manufactured from a liquid phase, and other layers (e.g. hydrogel) can also be introduced.

Opening 5 is left open after the solution has been introduced into the containment. The wafer, provided with depressions, is left in a dust-free atmosphere until the solvent evaporates, leaving a solidified membrane 7.

As will be evident from FIG. 1, the active surface of the membrane that occupies opening 6 is very small, whereas the membrane's total volume is very large. The eventual result will be a slight impoverishment of the ionophore in membrane 7. The specific geometry of the containment will also promote micromechanical anchoring of the membrane.

Figure 2:
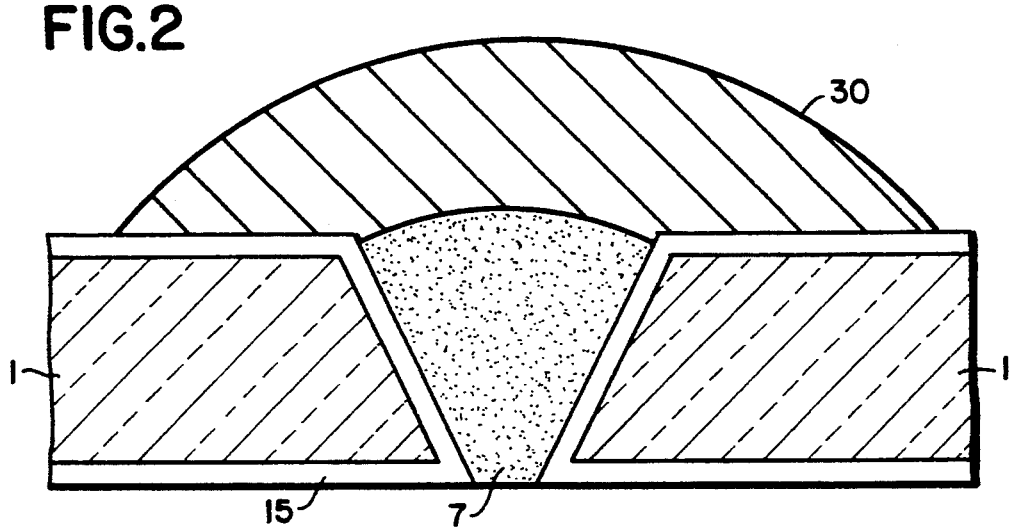

FIG. 2 illustrates another embodiment of the invention. The chip is similar to that illustrated in FIG. 1 and its containment is occupied by a membrane. In this version, however, the containment is blanketed with a protective layer 30 of epoxide or silicone for example. It is of course also possible to blanket not just such a small area but the whole chip or even the entire wafer with such a layer to seal off the containments before it is divided into chips with such a coating.

Figure 3:
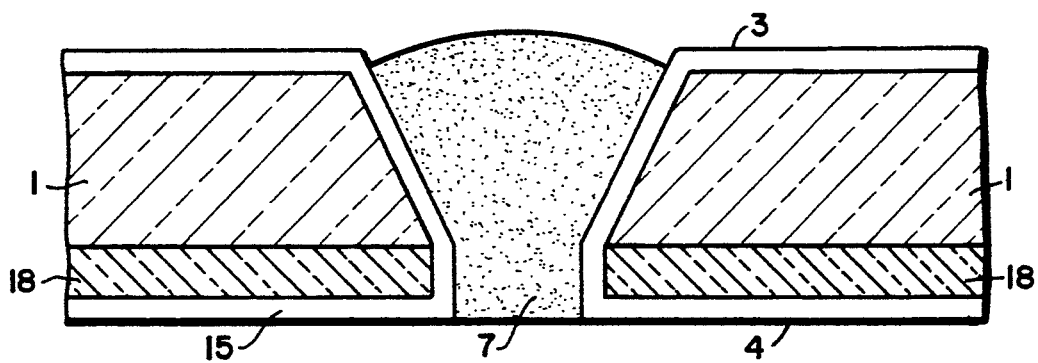

FIG. 3 illustrates how the geometry of the containment can be very precisely controlled in the vicinity of the small opening in the bottom of the chip by applying a layer 18 of resist on the bottom of the chip that will bring the etching process to a halt. Such a resist will contain a high proportion of boron for example (Heuberger, op. cit., pp. 151 and 141–1459).

The smaller opening in the containment can then be opened from the back for example by further masking and etching, and the membrane introduced and blanketed as hereintofore described.

Figure 4:
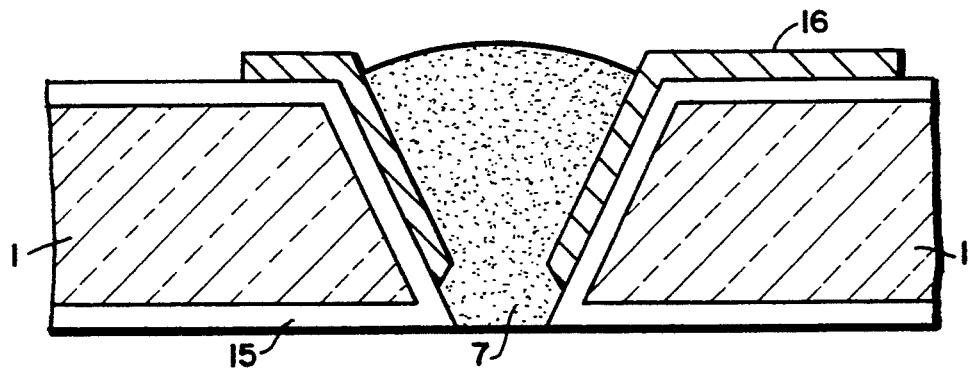

FIG. 4 illustrates how such a containment can be produced by a modification of the coated-film principle. A wafer 1 is coated with a layer of insulating and optionally silanized silicon dioxide or other insulating layer. The wafer is then provided with a thin film, in the form of a funnel or strip in the vicinity of the depression, of metal by known techniques of masking and vapor deposition or sputtering. The metal can be silver, silver chloride on silver, or such another conductor as platinum or gold. The metal constitutes an electric connection between membrane 7 once it has been introduced and an unillustrated integrated circuit on the same chip.

The vapor-deposited or sputtered-on silver film can be chemically or galvanically chlorided by the known method for example.

Figure 5:
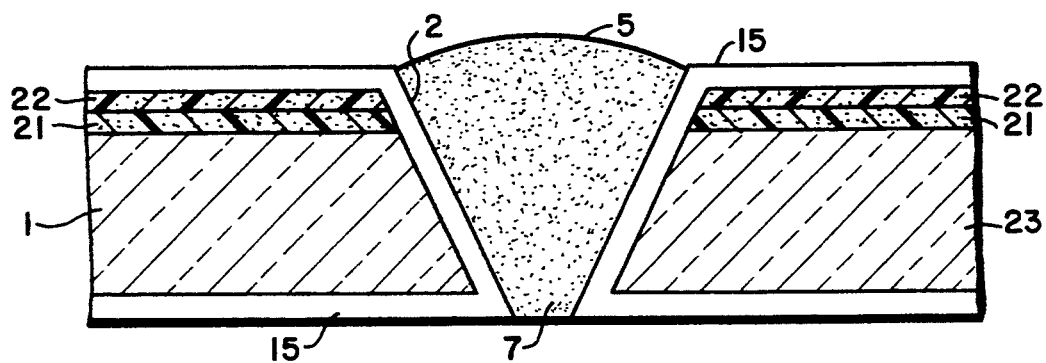
FIG. 5 a VISFET (vertical ion-selective field-effect transistor)
Figure 6:
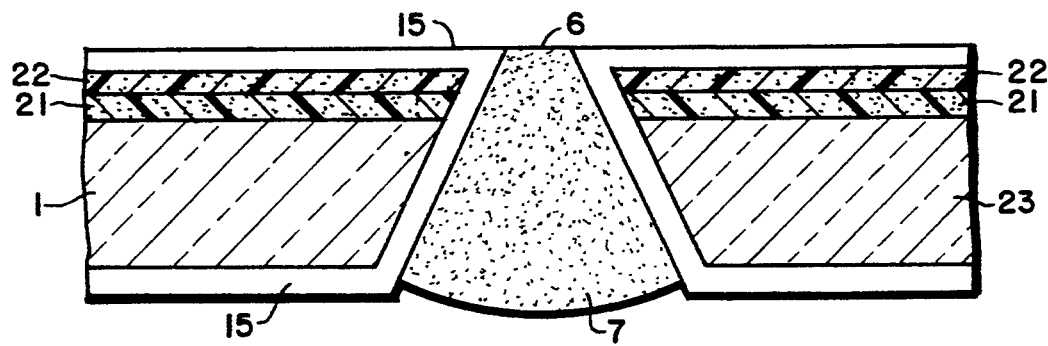
FIG. 6 another type of VISFET.

Another application of the method in accordance with the invention involves using the aforesaid containments as bases for the manufacture of sensor components that operate in accordance with the ISFET principle. This application is based on a novel principle, that of a vertical ion-selective field-effect transistor (VISFET). Such a transistor can have various designs. FIGS. 5 and 6 illustrate two.

A silicon-crystal wafer is anisotropically etched as hereintofore described (cf. FIG. 5), resulting in a depression 2 in the form of an inverted truncated pyramid if the silicon is oriented (100). When (110)-oriented silicon is employed, the masks must be adjusted to produce a depression 2 with two parallel perpendicular walls and two sloping walls. If the distance between the two parallel walls is very short, very little of the chip's real estate will be occupied. The section in FIG. 5 would in this event parallel the perpendicular walls of the containment.

The containment is produced in a substrate 1, previously provided like a VMOSFET (Paul, op. cit., p. 336) with a highly n-doped source layer 22, a p-doped layer 21 for the channel area, and an n-doped drain layer 23. The vicinity of the drain can, as illustrated in FIG. 5, be silicon substrate 1 itself. It is, however, also possible as with a VMOSFET, to epitaxially generate an additional layer on the substrate. A solution that will form the ISE membrane is then introduced into depression 2 and left until the solvent evaporates, leaving a membrane 7.

The channel area in this embodiment is in the vicinity of wider opening 5. It is also possible to stack the layers such that channel area 21 will be in the vicinity of smaller opening 6 (FIG. 6). The gate dielectric consists as in known ISFET's for example of a layer of $SiO_2$ or of a sequence of layers of $SiO_2$ and $Si_3N_4$. the larger containment opening can, once the ion-selective membrane has formed, be blanketed with a protective coating as illustrated in FIG. 2.

Membrane 7 always constitutes what is called the VISFET's gate. In addition to the "impoverishing" version specified herein, the ISFET can also be of an "enriching" type or have a reversed polarity (negative for positive).

The structures illustrated in FIGS. 5 and 6 are also appropriate for VISFET's with a solid membrane plus an electrochemically relevant layer 7 instead of the liquid membrane. Dielectric layer 15 can be constituted consequent to a layer of $SiO_2$ or other solid (e.g. $Si_3N_4$, $Ta_2O_5$, etc.) on top of the silicon. The extra layer can for example be vapor-deposited or sputtered over the $SiO_2$ or applied sol-to-gel. It acts as an ion-selective solid membrane.

When two similar VISFET's of this type are produced on the same silicon chip, it is possible to provide only one with an extra layer 7. The layer can consist of hydrogel for example, which will considerably delay the response of the solid membrane beneath it. The combination of VISFET structures with and without a layer 7 of hydrogel will make it possible to measure difference in the known way.

The aforesaid ion-selective sensor components with micromechanically structured containments can also be modified to operate with a solidified interior-electrolyte layer in accordance with the half-cell principle.

Figure 7:
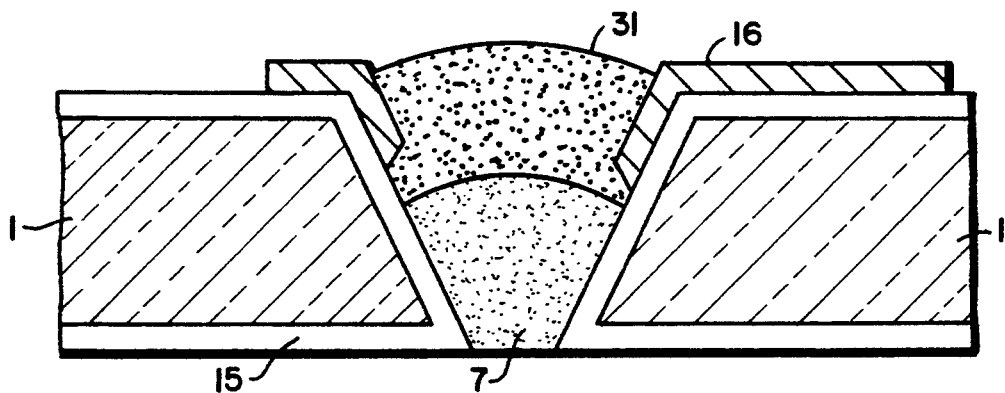
FIGS. 7 and 8 two different versions of an ion-selective sensor component in accordance with the half-cell principle, FIG. 9 a VISFET with an interior electrolyte, FIG. 10 a sensor component with capillary channel and filling opening, FIG. 11 a capillary-channel structure for supplying liquid membrane material to the containments, and FIG. 12 a sensor chip in a housing.
Figure 8:
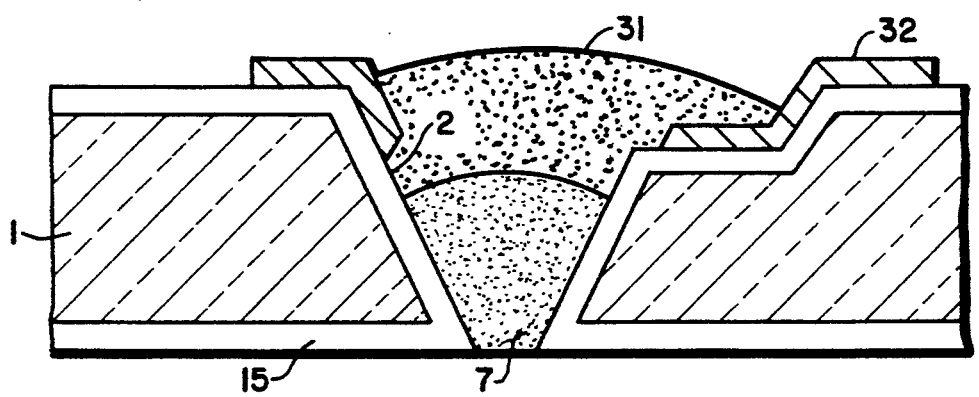

FIGS. 7 and 8 illustrate two different versions. The version illustrated in FIG. 7 differs from the one illustrated in FIG. 4 only in that diversion electrode 16 does not extend as far into the containment and in that there is a solidified interior-electrolyte layer 31 over ion-selective liquid membrane 7. The diversion electrode can for example be a film of silver chloride on silver.

Once the ion-selective liquid (e.g. polyvinyl chloride) membrane has been introduced into the containment and solidified therein as hereintofore described, the interior electrolyte can be poured over it in a separate procedure. The electrolyte can, like known electrolytes, be a solution of salt (e.g. potassium chloride) treated with gelatin, agar-agar, or polyvinyl alcohol to result some time after the originally liquid interior electrolyte has been introduced in a solidified interior-electrolyte layer in the containment and on top of the ion-selective liquid membrane.

FIG. 8 illustrates another version that differs from the aforesaid embodiments in that it has a small containment 32 in addition to and directly communicating with large containment 2. Smaller containment 32 is also produced by anisotropic etching. This version facilitates separating the liquid membrane and interior electrolyte.

Figure 9:
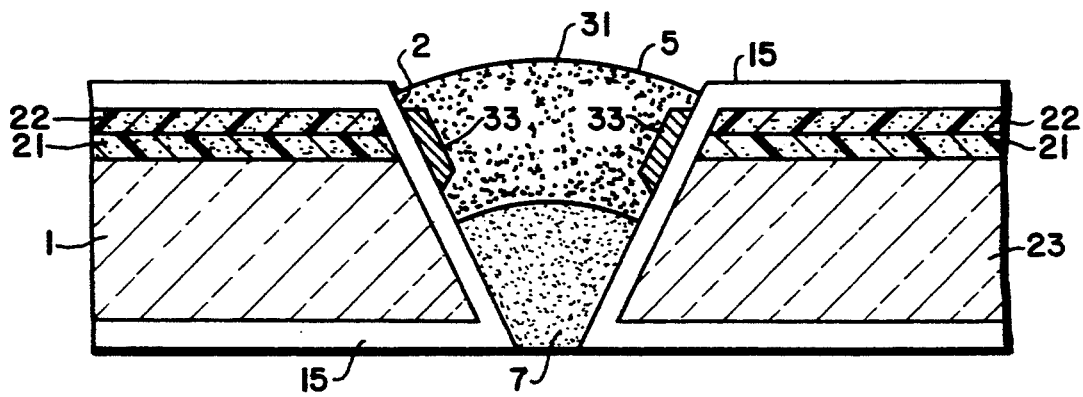

It is also possible to manufacture VISFET structures with interior electrolytes (FIG. 9). This embodiment differs from that illustrated in FIG. 5 in that a layer 33 of silver has been vapor-deposited or sputtered over dielectric layer 15 for example, lithographically structured, and covered with silver chloride. The containment has, like the one illustrated in FIG. 8, a liquid membrane 7 and an interior electrolyte 31.

The introduction of membrane solutions and other liquids to obtain electrochemically relevant layers can be facilitated by means of capillay channels. The channels are, like the containments, anisotropically etched and can have V-shaped or U-shaped cross-sections.

Figure 10:
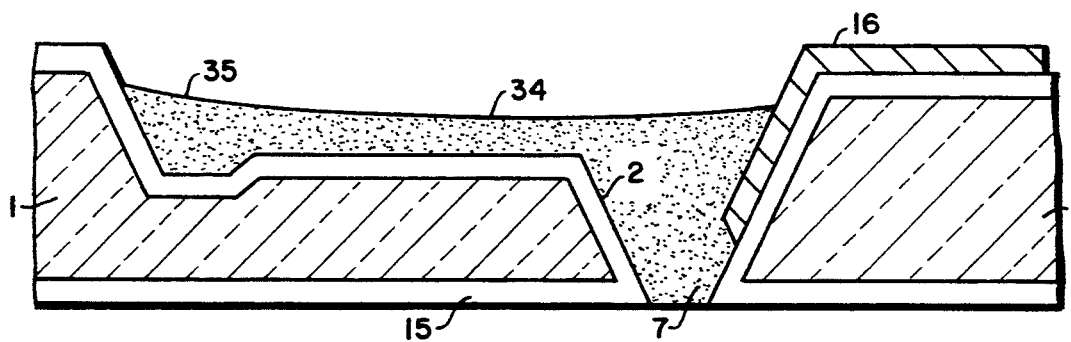

FIG. 10 is a section similar to FIG. 4 and illustrates by way of example an embodiment with a capillary channel 34 and a filling opening 35. The membrane liquid is introduced through the filling opening and forwarded to the containment through the channel by capillary action. It is also possible to supply all the containments in adjacent chips or all the containments in a single wafer with liquid from one filling opening. The filling opening can then be eliminated when the chips are isolated. The flow of membrane solution can be improved by introducing it in a solvent atmosphere.

Figure 11:
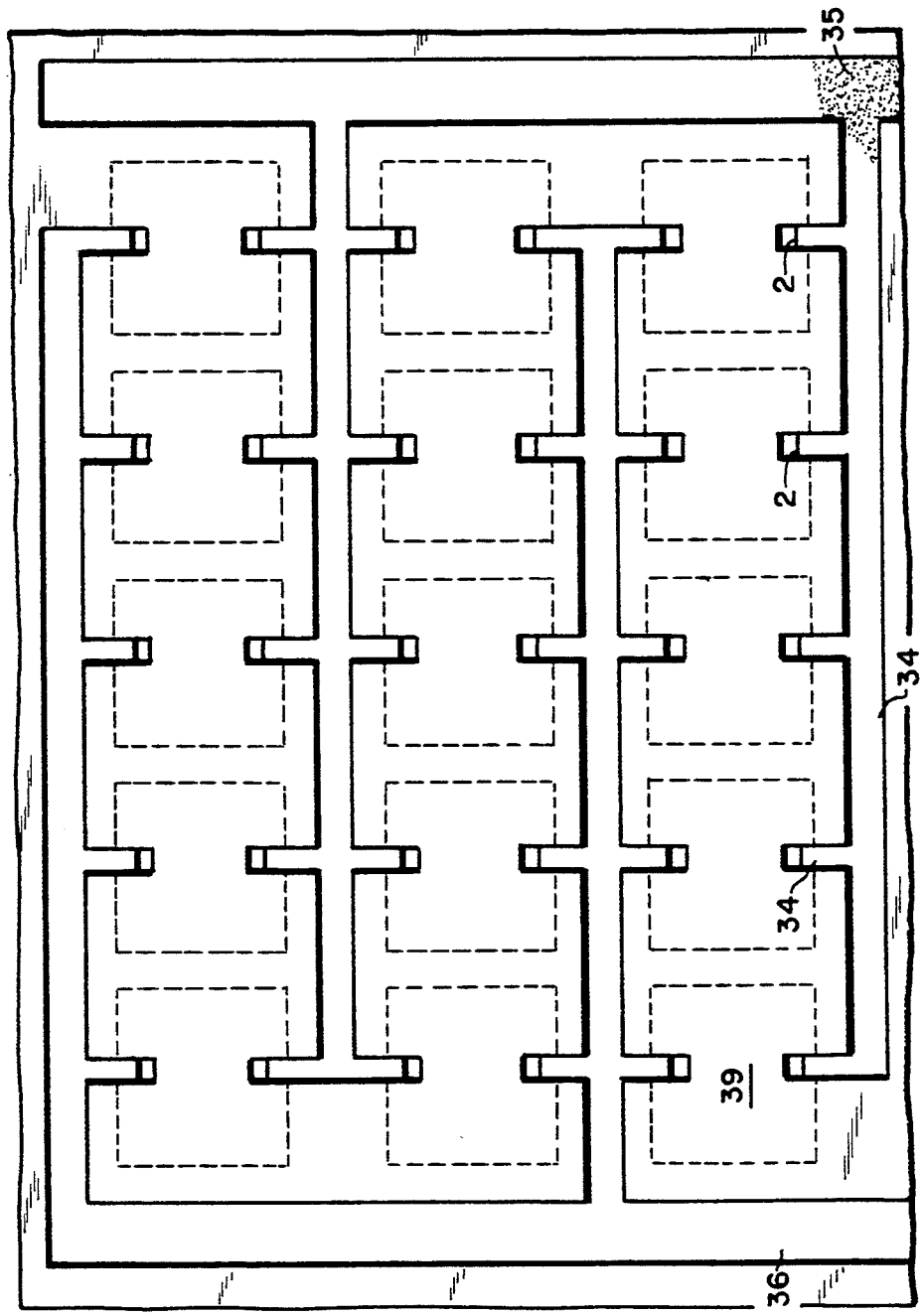

FIG. 11 illustrates a system of capillary channels 34 and filling openings 35. There is a sensor-component chip 39 and containment 2 at the end of every capillary channel.

Figure 12:
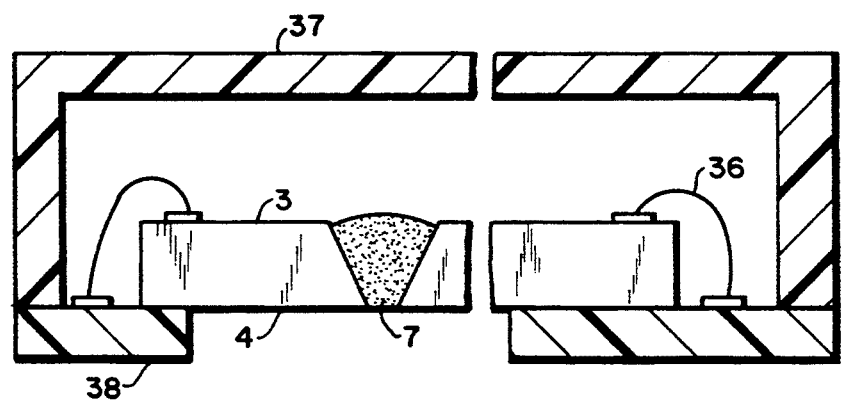

FIG. 12 illustrates a silicon chip with an ion-selective membrane 7 in a containment with its active surface at the back 4 of the chip. The chip's contact areas are on top or front 3 and connected to the housing contacts by fine bond filaments 36. The illustrated upper housing component 37 can be replaced by a support 38, and the total chip can be on top with plastic.

There has thus been shown and described a novel method of manufacturing miniaturized components of chemical and biological detection sensors that employ ion-selective membranes which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

I claim:

1. In a method of manufacturing supports for miniaturized components of sensors that detect chemicals and biologicals by means of ion-selective membranes, said method comprising the following steps:
   (a) producing a thin substrate of a single-crystal silicon having a front side and a back side and having one of a (100) and a (110)-orientation in its plane,
   (b) etching said substrate anisotropically from the front side to the back side, thereby forming an opening that tapers from the front side to the back side in the form of a truncated pyramid, when etched in a silicon substrate having a (100)-orientation, and an opening with two parallel as well as perpendicular walls and two sloping walls when etched in a silicon substrate having a (110)-orientation, said opening forming a containment; the improvement wherein
   (1) at least one electrode is applied against one of the internal walls of the opening;
   (2) a liquid solution is introduced into the containment from the front side, said solution comprising one of a polymer in a solvent which is allowed to evaporate and a solution which is allowed to solidify into an hydrogel; and
   (3) leaving the solidified polymer or hydrogel as ion-selective membrane within the containment and with contact with the electrode.

2. Method as in claim 1, wherein the containment is anisotropically etched in the form of a truncated pyramid into a (100)-oriented silicon substrate.

3. Method as in claim 1, wherein the containment is anisotropically etched into a (110)-oriented silicon substrate, generating an opening with two parallel and perpendicular walls and two sloping walls.

4. Method as in claim 1, wherein the back of the silicon substrate is provided with a layer of resist before being anisotropically etched, wherein the containment is then etched through from the front to the resist, and wherein the layer of resist is then etched through to the back of the substrate where the opening narrows.

5. Method as in claim 1, further comprising the step of providing the containment, at least in the vicinity of its opening on the front and of its opening on the back along with the opening's internal walls, with a continuous layer of silicon dioxide.

6. Method as in claim 5, further comprising the step of silanizing the layer of silicon dioxide that constitutes the phase interface with the ion-selective membrane.

7. Method as in claim 5, further comprising the step of providing a second layer in addition to the layer of silicon dioxide on the internal walls of the containment.

8. Method as in claim 7, wherein said second layer is $Si_3N_4$.

9. Method as in claim 5, wherein said layer of silicone dioxide is provided by a process selected from the group consisting of thermal oxidation, chemical-vapor deposition and sol-to-gel condensation.

10. Method as in claim 1, wherein the electrode is applied by a process selected from the group consisting of vapor deposition and sputtering and is a lithographically structured film.

11. Method as in claim 10, wherein said structured film is formed of a material selected from the group consisting of silver, silver chloride over silver, platinum and gold.

12. Method as in claim 10, wherein the filling opening and the capillary channel are blanketed with a protective coating.

13. Method as in claim 1, wherein the liquid introducing step includes the step of introducing a solution, containing a polymer in a solvent, into the containment and allowing the solvent to evaporate, leaving the solidified polymer of liquid membrane.

14. Method as in claim 13, wherein the liquid membrane produced is polyvinyl chloride.

15. Method as in claim 1, wherein the liquid introducing step includes the steps of introducing a solution into the containment and allowing the solution to solidify into an electrochemically relevant layer.

16. Method as in claim 15, wherein the electrochemically relevant layer is a hydrogel.

17. Method as in claim 1, wherein the liquid introducing step includes the steps of introducing a solution into the containment and allowing the solution to solidify into a membrane with a biochemically active material embedded in it.

18. Method as in claim 17, wherein the biologically active material is an enzyme.

19. Method as in claim 1, further comprising the steps of applying a solidified interior-electrolyte layer over the ion-selective membrane in the containment and connecting the same to a diversion electrode.

20. Method as in claim 19, wherein the solidified interior-electrolyte layer is connected to a gate contact.

21. Method as in claim 20, wherein the gate contact is formed by a layer of silver chloride over silver.

22. Method as in claim 1, wherein the containment communicates through a capillary channel with a filling opening and wherein the membrane liquid is a solvent that is introduced into the filling opening in a solvent atmosphere.

23. Method as in claim 22, wherein the silicon substrate forms a plurality of silicon chips each providing at least one containment, and wherein all the containments in adjacent chips are supplied with liquid from one filling opening and the chips are then isolated.

24. Method as in claim 23, wherein the chips are arranged in a single wafer, and are supplied with liquid from one filling opening on the wafer.

25. Method as in claim 1, wherein the front opening into the containment is blanketed with a protective coating.

26. Method as in claim 1, wherein the sensor component is accommodated in a housing and sealed off with a protective coating and wherein the active surfaces of the membrane are in contact with the fluid being analyzed at the rear of the chip.

27. A component for a sensor that detects chemicals and biologicals, manufactured by the method according to claim 1.

28. A method of manufacturing a vertical ISFET on a thin silicon substrate having a front side and a back side comprising the steps of (1) providing the front side of the silicon substrate with superimposed positive and negative layers constituting a source, drain and gate; (2) producing in the substrate an opening that tapers from the front side to the back side and provides communication and containment therebetween, and (3) introducing a-liquid into the containment opening to form an ion-selective membrane, wherein the containment is anisotropically etched, sloping together through the layers, and accommodates the ion-selective membrane, and wherein walls of the containment are provided with a dielectric layer.

29. Method as in claim 28, wherein the containment is etched through from the back of the substrate and wherein the small opening from the containment is positioned along with the active surface of the membrane at the front of the substrate.

30. Method as in claim 28, further comprising the steps of applying a solidified interior-electrolyte layer over the ion-selective membrane in the containment and connecting it to a diversion electrode.

31. Method as in claim 30, wherein said solidified interior-electrolyte layer is connected to the gate contact.

32. Method as in claim 31, wherein the gate contact is formed by a layer of silver chloride over silver.

33. Method as in claim 28, wherein the dielectric layer is a material selected from the group consisting of $SiO_2$ and $Si_3N_4$ over $SiO_2$.

* * * * *